US00PP16062P3

(12) United States Plant Patent
Zwagerman

(10) Patent No.: US PP16,062 P3
(45) Date of Patent: Oct. 25, 2005

(54) ***HOSTA* PLANT NAMED 'FIREWORKS'**

(50) Latin Name: ***Hosta* hybrid**
Varietal Denomination: Fireworks

(75) Inventor: Mary E. Zwagerman, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 13 days.

(21) Appl. No.: 10/735,102

(22) Filed: Dec. 12, 2003

(65) Prior Publication Data

US 2005/0132458 P1 Jun. 16, 2005

(51) Int. Cl.[7] ..... A01H 5/00

(52) U.S. Cl. ..... Plt./353

(58) Field of Search ..... Plt./353

*Primary Examiner*—Kent Bell

*Assistant Examiner*—Louanne Krawczewicz Myers

(57) ABSTRACT

A new and distinct *Hosta* plant named 'Fireworks', characterized by narrow pointed leaves having deep green margins, and a creamy yellow to creamy white center, that displays a unique upright habit and light lavender flowers held above the foliage on thick cream-colored scapes.

2 Drawing Sheets

Botanical classification: *Hosta* hybrid (Tratt.).
Variety denomination: 'Fireworks'.

BACKGROUND OF THE INVENTION

The present invention relates to the new and distinct cultivar of *Hosta*, botanically known as *Hosta* hybrid (Tratt.), and hereinafter referred to as the cultivar 'Fireworks'.

The new plant was discovered by the inventor, Mary Zwagerman as a non-induced, naturally occurring whole plant mutation of *Hosta* 'Loyalist' (not patented) in a greenhouse at a nursery in Zeeland, Mich., USA. Asexual propagation of the plant at the same nursery by tissue culture and division has shown that the unique and distinct characteristics of this new plant are stable and reproduce true to type in successive generations.

SUMMARY OF THE INVENTION

*Hosta* 'Fireworks' is unique from its parent sport, *Hosta* 'Loyalist' (not patented) and all other *hosta* cultivars known to the inventor, in several traits. *Hosta* 'Loyalist' is a tissue culture derived sport of *Hosta* 'Patriot' (not patented) which is a sport of *Hosta* 'Francee' (not patented). *Hosta* 'Francee' and 'Patriot' both have creamy white margins with the former having a thinner margin, and the latter, wider margins. *Hosta* 'Loyalist' (a reverse type variegation pattern) has a broader and flatter leave blade. *Hosta* 'Fireworks' has a narrower leaf, with a folded blade. 'Fireworks' is a more rapid grower than 'Loyalist', and reaches saleable size in a 3 inch×4½ inch deep pot in about 5½ months from a rooted cutting. *Hosta* 'Fireworks' has very thick, rigid leaves giving the whole plant an upright form and habit. The leaf blades and petioles have a wide dark green margin and yellowish cream to white centers. 'Fireworks' flowers in mid summer with light lavender flowers, on scapes above the foliage.

BRIEF DESCRIPTION OF THE DRAWINGS

The photographs of the new plant demonstrate the overall appearance of the plant including the unique traits. The colors are as accurate as reasonably possible with color reproductions. Some slight variation of color may occur as a result of lighting quality, intensity, wavelength, direction or reflection.

DETAILED BOTANICAL DESCRIPTION

Figure 1:
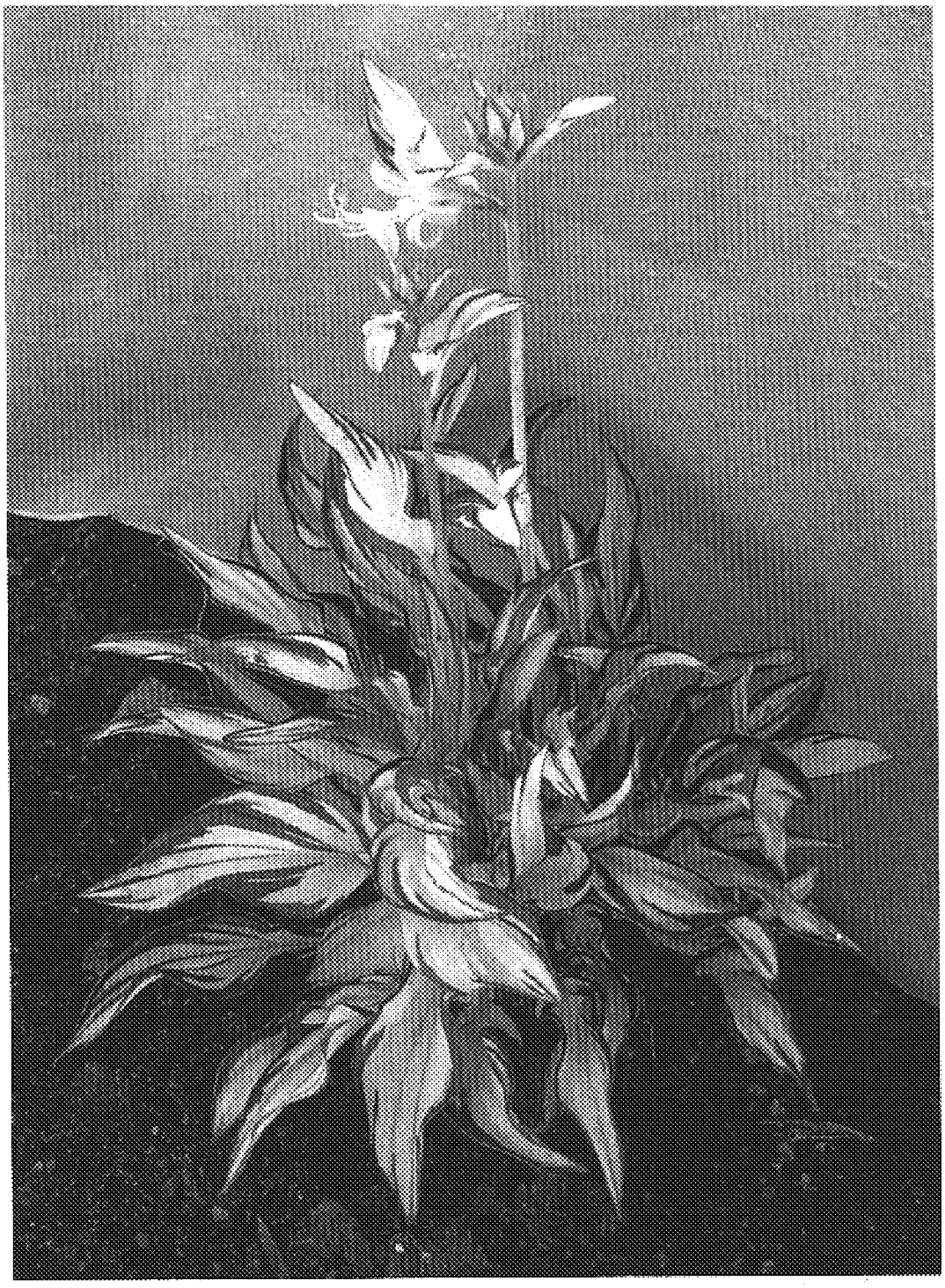
FIG. 1 shows the plant with scapes, flowers and buds.
Figure 2:
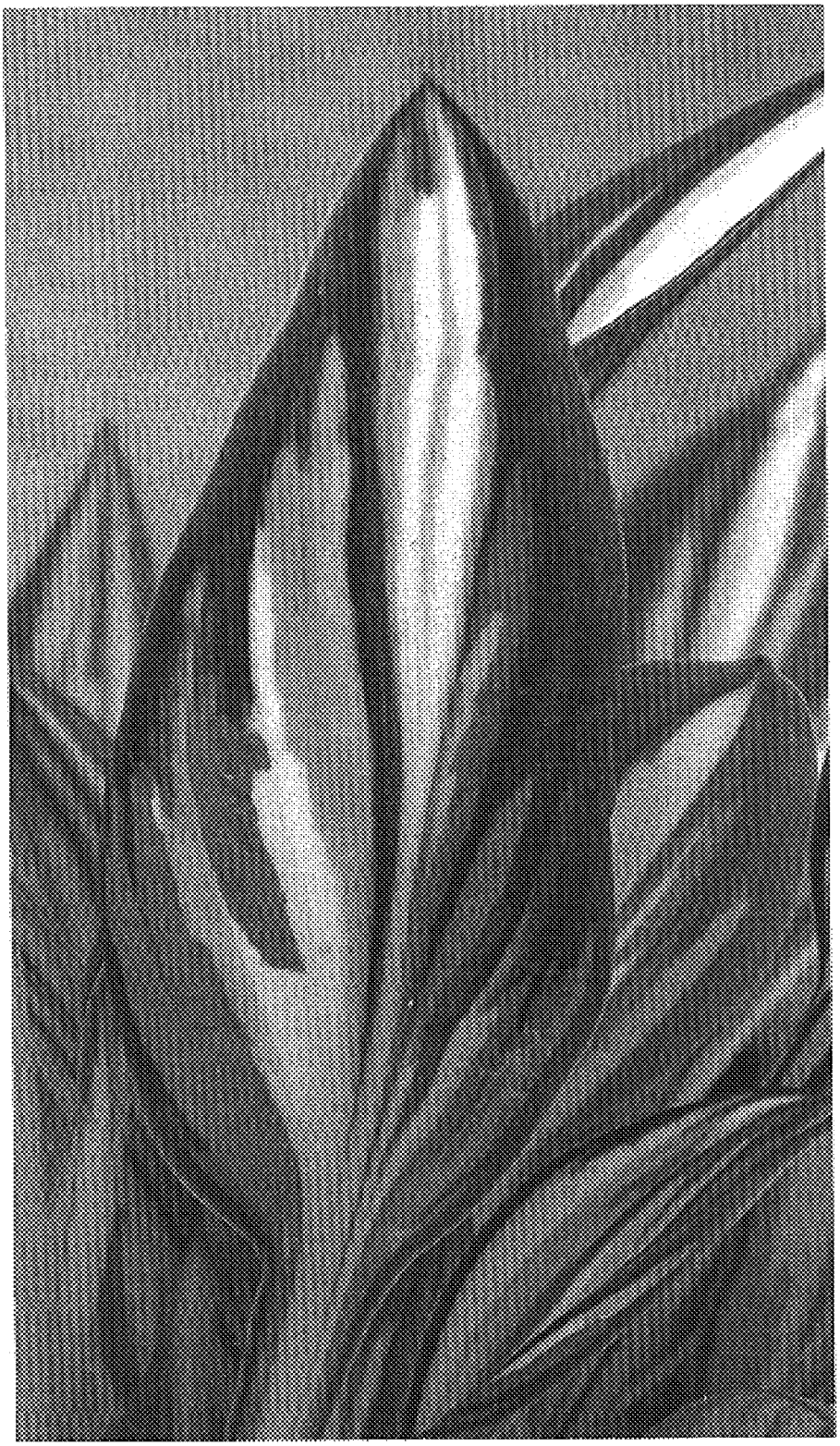
FIG. 2 shows a leaf with the intricate leaf colors.

The following descriptions and color references are based on The Royal Horticultural Society Colour Chart (2001 edition) except where common dictionary terms are used. The new plant, *Hosta* 'Fireworks', has not been observed under all possible environments. The phenotype may vary slightly with different environmental conditions, such as temperature, light, fertility and moisture, but without any change in the genotype. The following observations and size descriptions are of a three-year-old plant in a one gallon container grown in Zeeland, Mich., USA under 50% shade on cloudless days, day temperatures of 18 to 28 degrees C., and night temperatures of 15 to 20 degrees C.

Botanical classification: *Hosta* hybrid cultivar 'Fireworks'.

Parentage: Naturally occurring whole plant mutation of *Hosta* 'Loyalist' (not patented).

Propagation: Method by tissue culture and division. Time to initiate roots from both division and tissue culture about four weeks from cutting.

Rooting habit: Normal, fleshy, to 3 mm thick, branching.

Plant habit: Herbaceous, densely rhizomatous perennial, symmetrical with radical glabrous above and glaucous underneath leaves upright and erect through flowering period, more horizontal late in the season and in maturity.

*Crop time.*—Under normal summer greenhouse growing conditions about 22 weeks to finish in a one-liter container. Plant vigor is good.

*Plant size.*—Soil level to top of foliage at flowering is 18 to 24 cm tall and 25 to 30 cm wide.

Foliage description:

*Shape and size.*—Ovate to broadly ovate leaf blades have an acute apex and cordate base. The leaf blades are 13 to 16 cm long and 8 to 10 cm wide. The leaf blade margin is entire and the green variegation pattern on the edge varies in different regions of the leaf from 10 to 25 mm wide.

*Venation.*—Parallel, same color as surrounding leaf surface, either adaxial or abaxial.

*Color.*—Adaxial surface is a deep green closest to RHS 141 A on the margin of young emerging leaves. Later in the growing season, the margin is between RHS 139 A and RHS 136 A. As leaves are first emerging, the inside, or center portion of the leaf is yellow-green, more green than RHS 151 C. The center of the leaves then lightens to between yellow RHS 11 D to RHS 13 D later in the growing season.

Abaxial margin surface is RHS 137 B on early young leaves, and RHS 137 A on leaves later in the season. The abaxial center color starts RHS 154 D and lightens to RHS 4 D with light and heat as the season progresses. There are also three or more intermediate color patterns between the center and the margin. The main intermediate color band on the adaxial surface is yellow-green RHS 144 B on newly emerged leaves, and between RHS 143 B and RHS 143 C on older leaves. Other more yellow, lighter, or more grayed bands including: RHS 138 B, RHS 138 D, RHS N144 D and RHS 143 A are also sometimes present in thinner and shorter stripes. The main intermediate band visible on the abaxial side is RHS 144 C on young leaves and about RHS 145 C on leaves later in the season. The thinner and shorter bands on the abaxial side sometimes include RHS 144 D, RHS 145 C, RHS 145 D and 141 D. Petioles are 18 to 22 cm long and 6 to 9 mm wide. The center color starts the same as the leaf center and lightens to RHS 11 D, but varies like the leaves depending on how much light the petiole receives. The edge of the petiole is green RHS 136 A on both surfaces.

Flower description:

*Bud.*—Torpedo-shaped, flared at apex; two days prior to opening the buds are violet RHS 85 D and RHS 85 A, 6 to 7 cm long, up to 1.5 cm wide, and when opened the flowers have tepals of Red purple RHS 69D and violet stripes of RHS 84 B.

*Flowers.*—15 to 21 per scape, 4 to 6 scapes per plant; funnelform, 4 to 6 cm wide and 6 to 8 cm long, (distal flowers being smaller) subtended by a bract, simple, entire, narrowly-acute, sessile, with base wrapped around scape, up to 2 cm long and 5 to 7 mm wide with the same colors and pattern as the leaves; flowers persist for a normal period, up to two days on or off the plant, and the scapes remain effective from mid July to late August. No fragrance has been detected.

*Peduncle.*—Erect to 48 cm tall and 0.8 cm in diameter, cream color RHS 11 D with tints of green lighter than RHS 139 D closer to the base, and a reddish purple stippling RHS 60 B becoming much heavier at the apical one fifth.

*Pedicel.*—Approximately 1 cm long, 3 mm wide, between RHS 76 C and RHS 76 D.

*Tepal.*—Six, simple, entire, fused at the base, oblong to elliptic, with slightly-recurved acute apex, approximately 7 cm long and 1.2 cm wide, arranged in two layers of three, the inner three with clear 1 to 2 mm margin, main adaxial color in center of tepals is Red purple RHS 69D and violet stripes of RHS 84 B. Abaxial color of the tepals is between RHS 75 B and 76 B without obvious stripes except for the clear margin.

*Gynoecium.*—Single, style — 5 to 6 cm long, 1 mm diameter, near white, curled upward at distal end; Stigma — entire, white, up to 3 mm diameter.

*Androecium.*—Filaments — six, white, approximately 1 mm in diameter and up to 5 cm long.

*Anthers.*—5 to 6 mm long, 1.5 mm wide, about RHS 83 A around margin of abaxial side, white in center, pollen is yellow-orange RHS 17 B. Seeds have not been observed.

Disease resistance: The plant is more resistant to melting-out than most other light-centered varieties, a condition where the light colored leaf center becomes necrotic. It grows best with plenty of moisture but is able to tolerate some drought. Hardiness to at least USDA zone 3, and other disease resistance is typical of other *hostas*. 'Fireworks' is more resistant to slugs and other pests than *hostas* with *Hosta plantaginea* lineage.

I claim:

1. A new and distinct cultivar of ornamental *Hosta* plant named 'Fireworks' as herein described and illustrated, suitable as a potted plant, for landscaping specimen or in mass, and for fresh-cut arrangements.

* * * * *